(12) United States Patent
Lal

(10) Patent No.: US 7,038,071 B2
(45) Date of Patent: May 2, 2006

(54) PLATINUM COMPOUNDS

(75) Inventor: Manjari Lal, Bellevue, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 65 days.

(21) Appl. No.: 10/622,007

(22) Filed: Jul. 16, 2003

(65) Prior Publication Data

US 2004/0092585 A1 May 13, 2004

Related U.S. Application Data

(60) Provisional application No. 60/396,299, filed on Jul. 16, 2002.

(51) Int. Cl.
*C07F 15/00* (2006.01)
*A61K 31/28* (2006.01)

(52) U.S. Cl. ..................... 556/136; 514/492
(58) Field of Classification Search ............ 514/492; 556/136
See application file for complete search history.

(56) References Cited

U.S. PATENT DOCUMENTS

| | | | |
|---|---|---|---|
| 4,140,707 A | 2/1979 | Cleare et al. | |
| 4,177,263 A | 12/1979 | Rosenberg et al. | |
| 5,117,022 A | 5/1992 | Khokhar et al. | |
| 5,648,384 A | 7/1997 | Kidani et al. | |
| 5,922,689 A | 7/1999 | Shaw | |
| 6,001,817 A | 12/1999 | Shaw | |
| 6,011,166 A | 1/2000 | Valsecchi et al. | |
| 6,130,245 A | 10/2000 | Shaw | |
| 6,194,403 B1 | 2/2001 | Hu et al. | |
| 6,297,245 B1 | 10/2001 | Shaw | |
| 6,331,559 B1 | 12/2001 | Bingham et al. | |

FOREIGN PATENT DOCUMENTS

WO    WO 00/63219 A1    10/2000

OTHER PUBLICATIONS

Leonetti, C., et al., "α-Tocherol Protects Against Cisplatin-Induced Toxicity Without Interfering With Antitumor Efficacy," *Int. J. Cancer* 104(2):243,250, 2003.

Manzotti, C., et al., "BBR 3464: A Novel Triplatinum Complex, Exhibiting a Preclinical Profile of Antitumor Efficacy Different from Cisplatin," *Clinical Cancer Res.* 6:2626-2634, Jul. 2000.

Martin-Ramos, J.D., et al., "Copper(II) and Nickel(II) Chelated With Dihydrogen Trans-1,2-Diaminocyclohexane-N,N,N'N'-Tetraacetate(2-) Ion ($H_2CDTA^{2-}$). Synthesis, XRD Structure and Properties of [Cu($H_2CDTA$)] $H_2O$ and [Ni($H_2CDTA$)($H_2O$)] $4H_2O$)", *Polyhedron* 15(3)439-446, 1996.

Pace, A., et al., "Neuroprotective Effect of Vitamin E Supplementation in Patients Treated With Cisplatin Chemotherapy," *J. Clin. Oncol.* 21(5):927-391 Mar. 2003.

(Continued)

*Primary Examiner*—Porfirio Nazario-Gonzalez
(74) *Attorney, Agent, or Firm*—Christensen O'Connor Johnson Kindness PLLC

(57) ABSTRACT

Platinum compounds, pharmaceutically acceptable salts, and prodrugs thereof. Compositions that include the platinum compounds, either alone or in combination with at least one additional therapeutic agent, with a pharmaceutically acceptable carrier. Methods for using the platinum compounds, either alone or in combination with at least one additional therapeutic agent, in the prophylaxis or treatment of proliferative diseases.

15 Claims, 8 Drawing Sheets

OTHER PUBLICATIONS

Akerley, W., et al., "Weekly, High-Dose Paclitaxel in Advanced Lung Carcinoma," *Cancer* 97(10):2480-2486, May 15, 2003.

Baumgartner, M.R. et al. "The Interaction of Transition Metals With the Coenzyme α-Lipoic Acid: Synthesis, Structure and Characterization of Copper and Zinc Complexes," *Inorganica Chimica Acta* 252:319-331, Nov. 1996.

Farrell, N., "Polynuclear Charged Platinum Compounds as a New Class of Anticancer Agents," in L.R. Kelland and N. Farrell (eds.), *Platinum-Based Drugs in Cancer Therapy*, Humana Press Inc., Totowa, New Jersey, Jun. 2000, pp. 321-339.

Fuertes, M.A., et al., "Novel Concepts in the Development of Platinum Antitumor Drugs," *Curr. Med. Chem.—Anti-Cancer Agents* 2(4):539-551, 2002.

Hegmans A., et al., "Novel Approaches to Polynuclear Platinum Pro-Drugs. Selective Release of Cytotoxic Platinum-Spermidine Species Through Hydrolytic Cleavage of Carbamates," *Inorg. Chem.* 40(24):6108-6114, Oct. 20, 2001.

Qu, Y., et al., "Synthesis, Characterization, and Cytotoxicity of Trifunctional Dinuclear Platinum Complexes: Comparison of Effects of Geometry and Polyfunctionality on Biological Activity," *J. Med. Chem.* 43(16):3189-3192, Jul. 20, 2000.

Serimaa, R., et al., "X-Ray Scattering Study on Amorphous, Polynuclear Platinum Uridine Complexes," *J. Am. Chem. Soc* 115(22):10036-10041, Nov. 3, 1993.

PLATINUM COMPOUNDS

CROSS-REFERENCE TO RELATED APPLICATION

This application claims the benefit of U.S. Provisional Application No. 60/396,299, filed Jul. 16, 2002, incorporated by reference herein.

FIELD OF THE INVENTION

The present invention relates to platinum compounds, compositions that include the platinum compounds, and methods for treating cancer using the platinum compounds.

BACKGROUND OF THE INVENTION

Cisplatin (cis-diaminedichloroplatinum(II), cis-DPP) is one of the most widely used drugs for the treatment of solid tumors and hematological malignancies (see Fuertes et al. (2002) *Curr. Med. Chem.—Anti-Cancer Agents* 2(4):539–551). However, there are several disadvantages associated with the administration of cisplatin, including adverse side effects (neurotoxity, nephrotoxicity, ototoxicity, and emetogenesis) and resistance (intrinsic and acquired). These disadvantages have motivated the search for new platinum anti-cancer agents with the following properties: (1) a broader spectrum of activity than cisplatin, particularly activity against cisplatin-resistant cancers; (2) an improved therapeutic index, either through greater efficacy or reduced toxicity; and/or (3) modified pharmacological properties to improve drug delivery.

Several new platinum anti-cancer compounds have been identified and are currently used in cancer chemotherapy, such as carboplatin (cis-diamine[1,1-cyclobutnaedicarboxylate(2-)-O,O'-platinum(II)) and oxaliplatin (cis-L-diaminocyclohexane oxalotoplatinum(II)). Carboplatin is less toxic than cisplatin, but also has less anti-cancer activity and is affected by the same resistance mechanism. Oxaliplatin circumvents cisplatin resistance, but its side effects include dose-limiting neurotoxicity.

Various polynuclear platinum complexes with anti-cancer activity have also been described and are currently in clinical trials, such as the BBR3464 (see U.S. Pat. No. 6,011,166; Manzotti et al. (2000) *Cancer Res.* 6:2626). However fewer than 1% of the platinum complexes tested for pre-clinical anti-cancer activity have entered clinical trials in the past 30 years (Fuertes et al. (2002) *Curr. Med. Chem.—Anti-Cancer Agents* 2(4):539–551).

Several studies in literature and clinical trials have indicated that administration of cisplatin results in oxidative stress and the production of reactive oxygen species such as free radicals. Oxidative stress reduces the rate of cell proliferation and is thought to interfere with the anti-cancer activity of cisplatin, which depends on the rapid proliferation of cancer cells for optimal activity. There is also evidence that the adverse side effects of cisplatin are caused by reactive oxygen species (see, e.g., Leonetti et al. (2003) *Int. J. Cancer* 104(2):243–50; Pace et al. (2003) *J. Clin. Oncol.* 21(5):927–31). Thus, there is a need for platinum anti-cancer compounds that elicit a reduced amount of oxidative stress.

SUMMARY OF THE INVENTION

The present invention provides platinum compounds, compositions that include the platinum compounds, and methods for treating cancer using the platinum compounds. The platinum compounds of the invention include cisplatin and carboplatin derivatives of tocopherols, folic acid, and lipoic acid.

In one aspect of the invention, platinum compounds are provided. In one embodiment, the invention provides platinum tocopherol compounds. Representative tocopherols include tocopherol succinate and tocopherol phosphate. In another embodiment, the invention provides platinum folic acid compounds. In another embodiment, the invention provides platinum lipoic acid compounds. In another embodiment, the invention provides polynuclear platinum complexes.

In another aspect, the invention provides compositions that include the platinum compounds. The compositions are useful for the administration of platinum compounds to treat cancer.

In another aspect of the invention, methods for treating cancer using the platinum compounds are provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention provides platinum compounds that are useful as therapeutic agents, methods for making the platinum compounds, and methods for their administration.

In one aspect of the invention, platinum compounds are provided. In one embodiment, the platinum compounds of the invention are cisplatin and carboplatin derivatives of tocopherols, folic acid, and lipoic acid. In another embodiment, the platinum compounds are polynuclear platinum compounds.

In one embodiment, the invention provides platinum tocopherol compounds. The platinum compounds of the invention include cisplatin tocopherol derivatives. These platinum compounds not only render cisplatin more lipophilic, thereby increasing its absorption and tumor cell membrane permeability causing the DNA repair machinery to be less efficient due to increased efficiency of the adduct formation in the DNA molecule, but because tocopherol is an antioxidant, the cisplatin tocopherol compound may reduce or prevent many of the side effects associated with the anticancer effects of chemotherapy.

Figure 1:
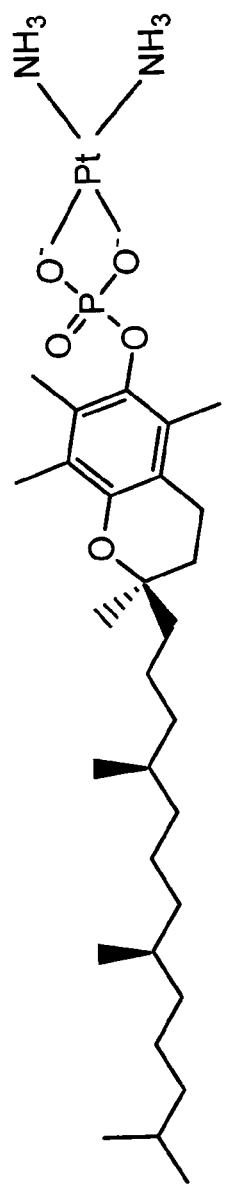
FIG. 1 illustrates the chemical structure of cisplatin tocopherol phosphate, a representative platinum tocopherol compound of the invention.

In one embodiment, the platinum tocopherol compound can be a tocopherol dicarboxylic acid derivative, for example, tocopherol succinate (e.g., vitamin E succinate). In another embodiment, the platinum tocopherol compound is platinum tocopherol phosphate. The syntheses of representative platinum compounds of the invention, cisplatin tocopherol succinate and cisplatin tocopherol phosphate, are described in Examples 1 and 2, respectively. FIG. 1 illustrates the chemical structure of cisplatin tocopherol phosphate.

In another embodiment, the invention provides platinum folic acid compounds. A major problem in cancer chemotherapy relates to enhancing the effectiveness of currently available anticancer drugs. Due to the lack of selectivity of the cytotoxic agents, the administration of single drug doses is restricted to sub-toxic levels. The problem is, therefore, how to attain sufficient amounts of drug at the tumor site for the required period of time without using drug doses that are above the threshold of toxicity. One possible solution to the problem is to use compounds with inherent or acquired ability to interact selectively with the target organ, thus leading to specific targeting to the tumor site, for example, anti-tumor antibodies. An alternative approach is to use targeting group, for example, folic acid, which binds to the overexpressed folate receptors on the cancer cell with specificity. A compound that includes a folic acid moiety may enhance the activity of the compound due to their specific, localized action at the target site.

Figure 2:
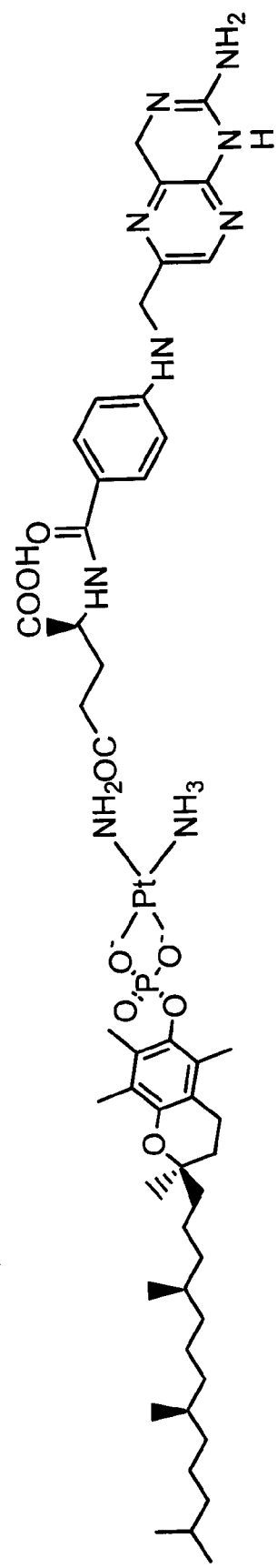
FIG. 2 illustrates the chemical structure of cisplatin tocopherol phosphate monofolate, a representative platinum tocopherol compound of the invention.
Figure 3:
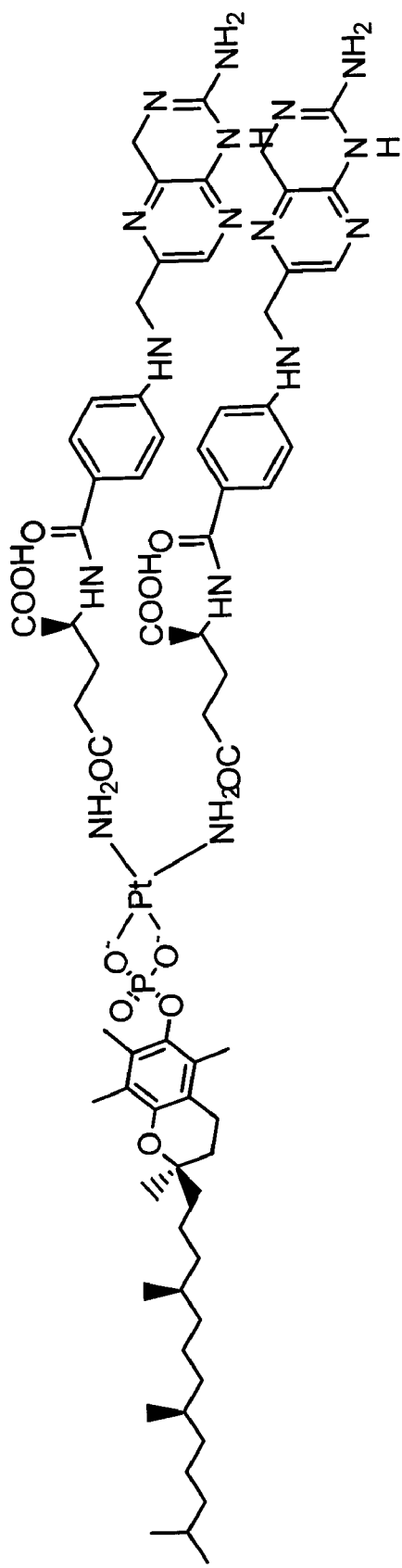
FIG. 3 illustrates the chemical structure of cisplatin tocopherol phosphate difolate, a representative platinum tocopherol compound of the invention.

In one embodiment, the platinum folic acid compound can be prepared by converting cisplatin tocopherol phosphate to a platinum monofolate compound. The platinum monofolate compound is illustrated in FIG. 2. Cisplatin tocopherol phosphate can also be converted to the corresponding platinum difolate compound. The platinum monofolate compound is illustrated in FIG. 3.

Figure 4:
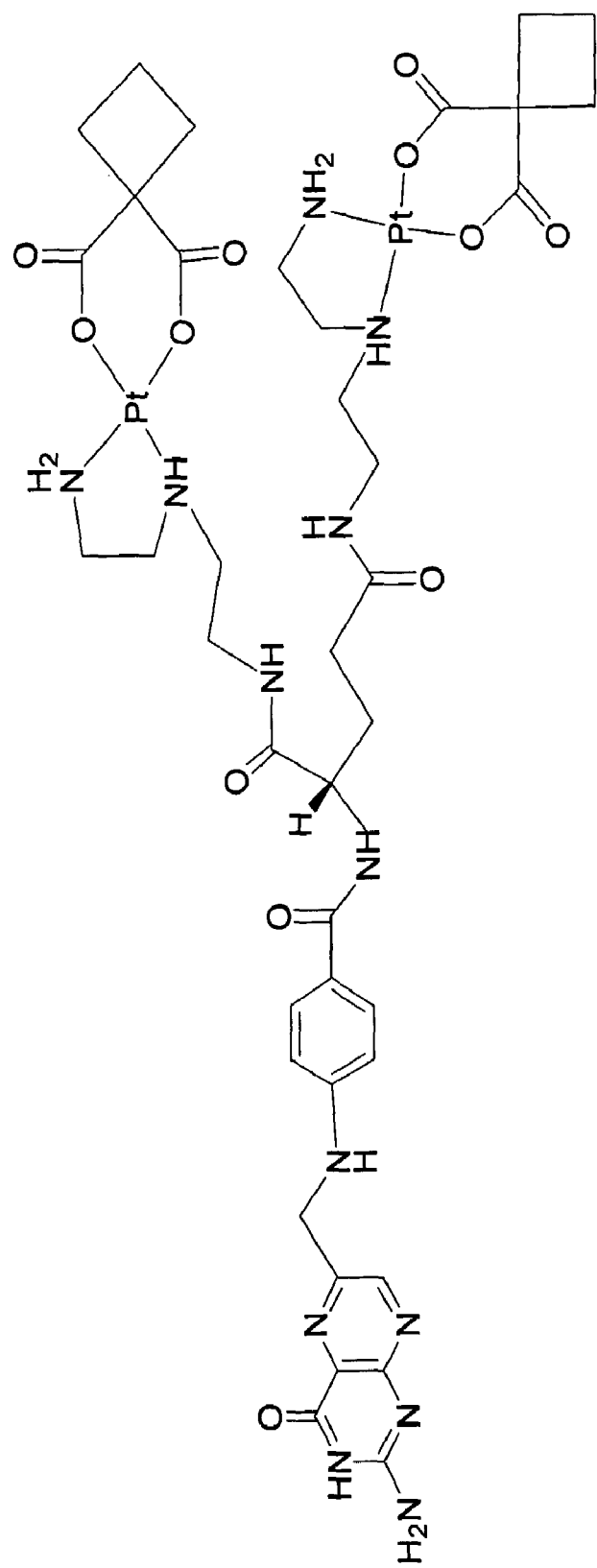
FIG. 4 illustrates the chemical structure of a carboplatin folic acid derivative including carboplatin groups, a representative platinum folic acid compound of the invention.

In another embodiment, the platinum folic acid compound can be prepared by converting folic acid to its N-hydroxysuccinimide ester, reacting the ester with diethylene triamine to provide a folate triamine, treating the folate triamine with potassium tetrachloroplatinate to provide a folate platinum chloride derivative, and then converting the platinum chloride derivative to a carboplatin derivative by reaction with 1,1-cyclobutanedicarboxylic acid sodium salt to provide a carboplatin difolate compound. The preparation of the carboplatin difolate compound is described in Example 3. The carboplatin difolate compound is illustrated in FIG. 4.

In another embodiment, the invention provides platinum lipoic acid compounds. In one embodiment, the platinum lipoic acid compound is a pegylated compound. In another embodiment, the platinum lipoic acid compound is a polynuclear platinum compound.

Alpha-lipoic acid (ALA, and also known as thioctic acid) works together with other antioxidants such as vitamins C and E. ALA is important for growth, helps the body produce energy, and aids the liver in removing harmful substances from the body. ALA also prevents cell damage, controls blood sugar, and removes toxic metals from the blood. In animal studies, ALA improved brain function as well. Because ALA is both water- and fat-soluble, it can function in almost any part of the body, including the brain. Unlike other substances, ALA can pass easily into the brain, and studies have shown that ALA has protective effects on brain and nerve tissue. ALA is promising as a treatment for stroke and other brain disorders involving free-radical damage. Animals treated with ALA had a four time greater survival rate after a stroke.

Clinical trials using cisplatin have demonstrated that cisplatin-induces peripheral neuropathy affecting the dorsal root ganglia and the peripheral sensory nerve axon. Cisplatin deposits at the dorsal ganglion and peripheral nerve continue to cause neurologic damage long after cisplatin administration is completed, possibly because these deposits impair cellular metabolism and axonal transport. Although cisplatin exerts its antitumor effects by binding with DNA and inhibiting DNA synthesis, evidence suggests that cisplatin's toxic effects may be associated with free radical-mediated damage caused by a cisplatin derivative-induced oxidation process. ALA has been shown to improve neuropathy without causing significant adverse effects by reducing oxidative stress from free radical formation and increasing antioxidant defense. Therefore, the platinum compounds of the invention that include lipoic acid moieties, unlike any other antioxidants, are believed to not only reduce the nephrotoxicity, but also the cisplatin induced neurotoxicity.

Figure 5:
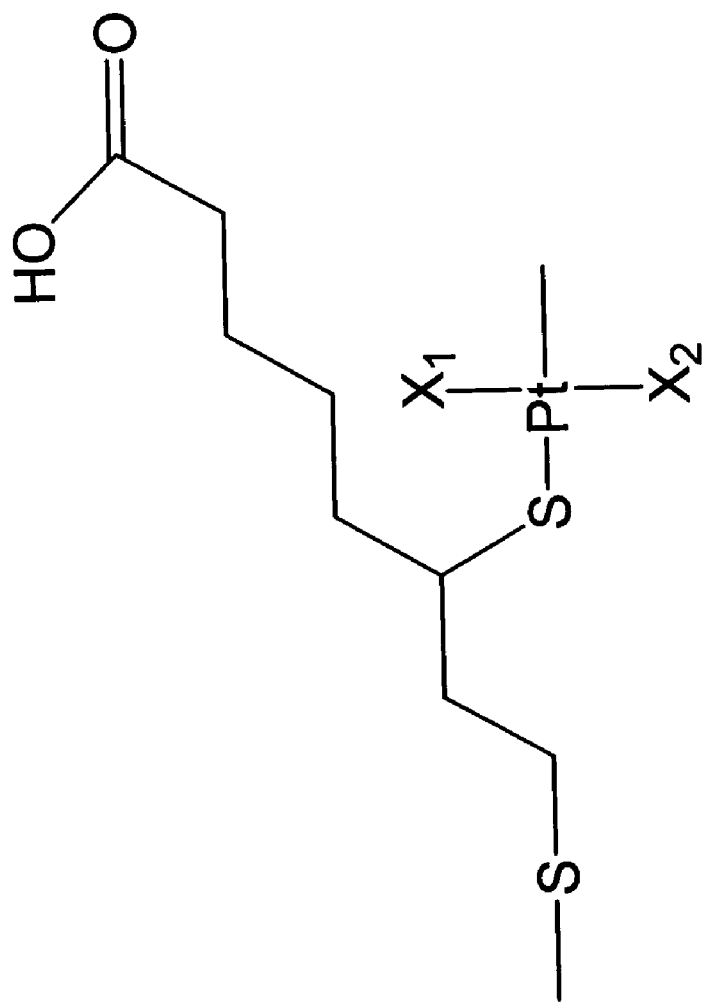
FIG. 5 illustrates the chemical structure of a platinum lipoic acid moiety of a representative polynuclear platinum compound of the invention.

As noted above, the invention provides a platinum lipoic acid compound that is a polynuclear platinum compound. As used herein, the term "polynuclear platinum compound" refers to a compound that includes two or more platinum atoms, preferably three or more platinum atoms. The polynuclear platinum compounds of the invention can be considered to be lipoic acid derivatives. The platinum compound includes two dihydrolipoic acid moieties bridged by a platinum atom through a sulfur atom from each dihydrolipoic acid moiety. In one embodiment, the polynuclear platinum compounds of the invention include a platinum lipoic acid moiety as illustrated in FIG. 5. Referring to FIG. 5, the platinum lipoic acid moiety includes platinum bonded to sulfur. The platinum lipoic acid moiety is bonded to the remainder of the compound through platinum and sulfur atoms. In FIG. 5, $X_1$ and $X_2$ are independently selected from Cl, $NH_2$, and OH. In one embodiment, $X_1$ is Cl and $X_2$ is $NH_2$. In one embodiment, $X_1$ is Cl and $X_2$ is OH. Carboxylic acid salts and carboxylic acid esters of the carboxylic acid illustrated in FIG. 5 are within the scope of this invention.

Figure 6:
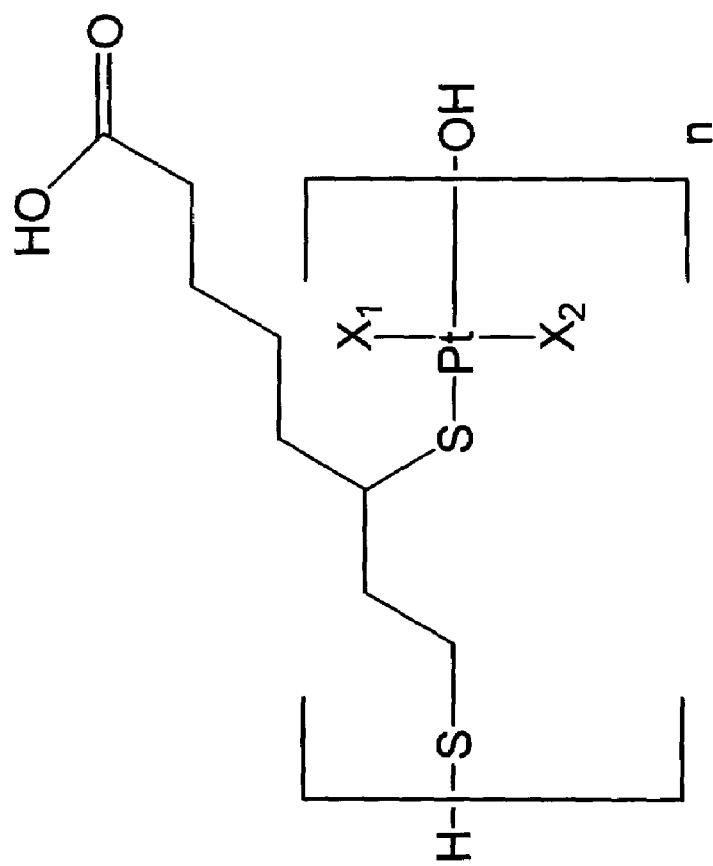
FIG. 6 illustrates the chemical structure of a representative polynuclear platinum compound of the invention.
Figure 7:
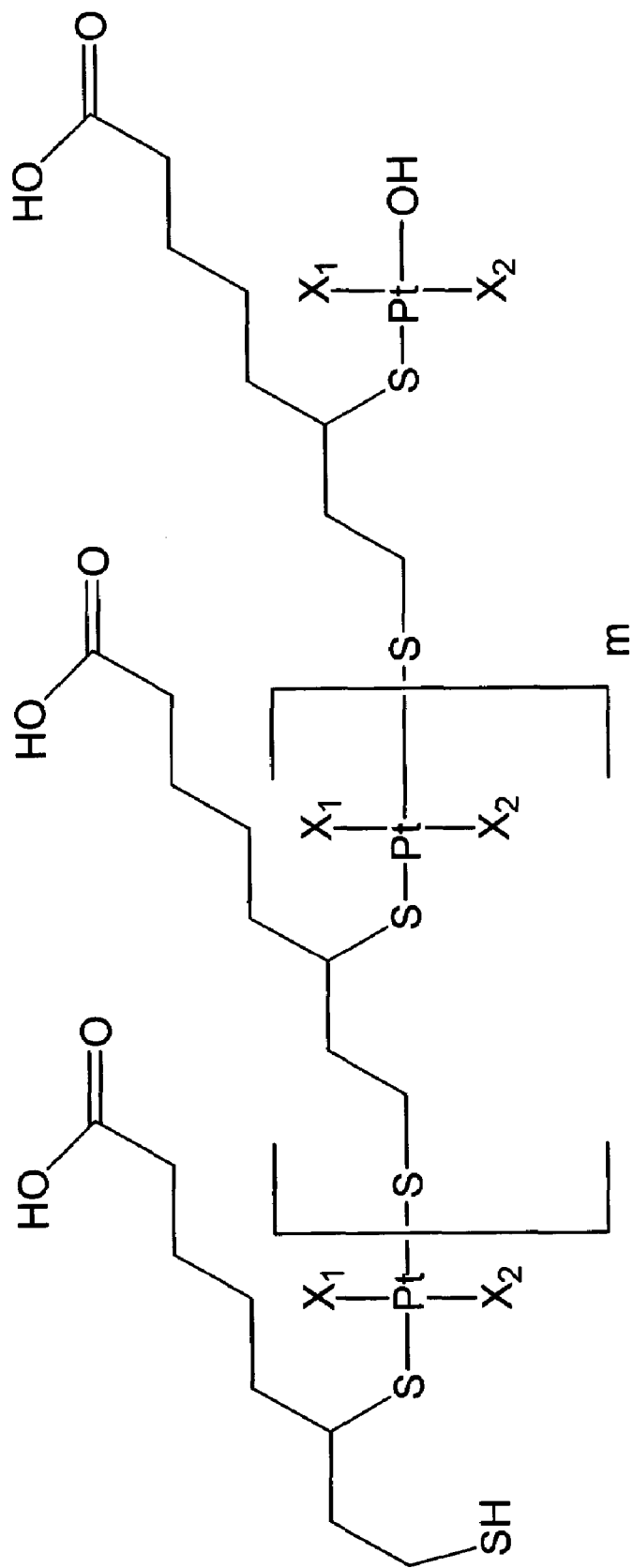
FIG. 7 illustrates the chemical structure of a representative polynuclear platinum compound of the invention.

Representative polynuclear platinum compounds of the invention are illustrated in FIGS. 6 and 7. The representative polynuclear platinum compounds illustrated in FIGS. 6 and 7 are polymers having a platinum lipoic acid repeating unit. In FIGS. 6 and 7, $X_1$ and $X_2$ are independently selected from Cl, $NH_2$, and OH. In one embodiment, $X_1$ is Cl and $X_2$ is $NH_2$ or OH. Carboxylic acid salts and carboxylic acid esters of the carboxylic acid groups illustrated in FIGS. 5, 6, and 7 are within the scope of this invention. Prodrugs of the platinum compounds are also within the scope of the present invention. FIG. 6 illustrates a polynuclear platinum compound having "n" platinum lipoic acid repeating units. For the polynuclear platinum compounds of the invention illustrated in FIG. 6, n=10–200. FIG. 7 also illustrates a polynuclear platinum compound having platinum lipoic acid repeating units. Depending on the synthetic method, the average molecular weight of the polynuclear platinum compound can be varied from about 5 kD to greater than about 100 kD.

The preparation and characterization of representative polynuclear platinum compounds of the invention are described in Example 4. The effectiveness of representative polynuclear platinum compounds in assays is described in Examples 5–8.

To understand the mechanism of action platinum compounds, the following discussion of cisplatin is illustrative. The biological activity of the anticancer drug cisplatin is believed to be mediated by its reactive hydrolysis product cis-diamineaquachloroplatinum(II) ion (monoaqua).

the invention have similar cytotoxic activities against cancer cells as cisplatin or carboplatin. Thus, representative platinum compounds of the invention have a $GI_{50}$ (as measured in mg of platinum per ml) in cancer cell lines that are in the same range as those observed for cisplatin and carboplatin, as shown in Example 5.

In some embodiments, administration of a therapeutically effective amount of representative platinum compounds of

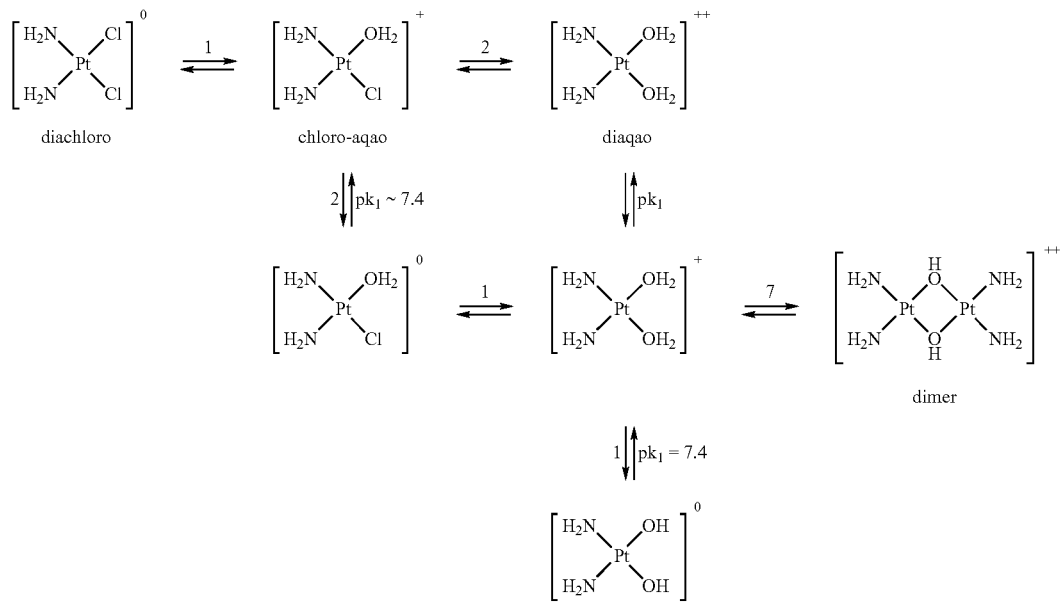

In the plasma at an extracellular chloride ion concentration of 0.15 M the predominant molecular species is the dichloro compound. This species is not charged and enters the cell via passive diffusion. In the cell, where the chloride ion concentration ⅟₂₀ that of the blood stream, significant amounts of the chloro-aquo species are formed. This molecule is charged and egress from the cell is therefore prevented. The formation of the chloro-aquo species in the body is slow and the half-life of (in vivo) reaction 1 at 37° C. is 3 hours.

Monochloro-aquo species is DNA reactive and forms a covalent bond with the N7 of adenine or guanine. This is called a monofunctional adduct. Over time, the second chloride is lost as aquation occurs and a second covalent bond is formed with another N7 of a different, but neighboring adenine or guanine. This is called a bifunctional adduct. The bifunctional adduct may be between two different strands of the DNA—an interstrand crosslink—or be located on the same strand of the DNA—an intrastrand crosslink. It takes about 4–6 hours to develop crosslinks in cells, indicating that platinum compounds behave as alkylating agents.

In another aspect, the present invention provides methods of treating human or animal subjects suffering from a cellular proliferative disease, such as cancer. The present invention provides methods of treating a human or animal subject in need of such treatment, comprising administering to the subject a therapeutically effective amount of a platinum compound of the invention, either alone or in combination with other therapeutic and/or anticancer agents. In some embodiments, representative platinum compounds of the invention causes fewer adverse side effects than administration of cisplatin. Cisplatin induces renal tubular damage leading ultimately to renal failure. Renal toxicity of cisplatin is manifested by an increase in serum creatinine, blood urea nitrogen (BUN), serum uric acid, and/or a decrease in creatinine clearance and glomerular filtration rate. Creatinine is a breakdown product of creatine, an important constituent of muscle. In the absence of renal disease, the excretion rate of creatinine is relatively constant. Elevated creatinine levels in plasma are an accurate indication of renal impairment. Urea is formed in the liver when the body breaks down protein, and circulates in the blood in the form of urea nitrogen. In the absence of renal disease, most urea nitrogen is filtered out by the kidneys and leaves the body in the urine. Renal impairment leads to elevated BUN levels. Administration of a therapeutically effective amount of representative platinum compounds of the invention does not cause nephrotoxicity or causes less nephrotoxicity than administration of cisplatin. For example, administration of representative platinum compounds of the invention produces no increases or smaller increases in serum creatinine levels and BUN levels than those produced after administration of cisplatin, as described in Examples 6–8.

In other aspects, the present invention provides methods for treating a cellular proliferative disease in a human or animal subject in need of such treatment, comprising administering to said subject an amount of a platinum compound of the invention effective to reduce or prevent cellular proliferation or tumor growth in the subject.

In yet other aspects, the present invention provides methods for treating a cellular proliferative disease in a human or animal subject in need of such treatment comprising administering to said subject an amount of a platinum compound of the invention effective to reduce or prevent cellular proliferation in the subject in combination with at least one additional agent for the treatment of cancer.

The platinum compounds of the invention, either alone or in combination with other anticancer agents, can be used for the prevention and treatment of cancers such as primary or metastatic melanoma, thymoma, lymphoma, sarcoma, lung cancer (NSCLC and SCLC), gastric cancer, liver cancer, non-Hodgkin's lymphoma, Hodgkins lymphoma, leukemias, testicular cancer, uterine cancer, cervical cancer, bladder cancer, kidney cancer, colon cancer, colorectal cancer, and adenocarcinomas such as breast cancer, prostate cancer, ovarian cancer, pancreatic cancer.

Compositions that include a platinum compound of the invention are administered to deliver effective amounts of the platinum compound. Effective amounts of the platinum compounds will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the platinum compounds of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the platinum compounds of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Platinum compounds that exhibit large therapeutic indices are particularly suitable in the practice of the methods of the invention. The data obtained from cell culture assays and animal studies may be used in formulating a range of dosage for use in humans or other mammals. The dosage of such platinum compounds lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The platinum compounds of the invention may be administered alone, or in combination with one or more additional therapeutically active agents. For example, in the treatment of cancer, the platinum compounds may be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxanes (e.g., paclitaxel, docetaxel). Appropriate amounts in each case will vary with the particular agent, and will be either readily known to those skilled in the art or readily determinable by routine experimentation.

Administration of the platinum compounds of the invention is accomplished by any effective route, e.g., parenterally or orally. Methods of administration include topical (for examples, skin patches), inhalational, buccal, intraarterial, subcutaneous, intramedullary, intravenous, intranasal, intrarectal, intraocular administration, and other conventional means. For example, the platinum compounds may be injected directly into a tumor, into the vicinity of a tumor, or into a blood vessel that supplies blood to the tumor.

In other aspects, the present invention provides pharmaceutical compositions comprising at least one platinum compound of the invention together with a pharmaceutically acceptable carrier suitable for administration to a human or animal subject, either alone or together with other therapeutics and/or anticancer agents. The platinum compounds of the invention may be formulated into a composition that additionally comprises suitable pharmaceutically acceptable carriers, including excipients and other compounds that facilitate administration of the platinum compounds to a mammalian subject. Further details on techniques for formulation and administration may be found in the latest edition of "Remington's Pharmaceutical Sciences" (Maack Publishing Co, Easton Pa.).

Compositions for oral administration may be formulated using pharmaceutically acceptable carriers well known in the art, in dosages suitable for oral administration. Such carriers enable the compositions containing platinum compounds of the invention to be formulated as tablets, pills, dragees, capsules, liquids, gels, syrups, slurries, and suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilising agents may be added, such as the crosslinked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Platinum compounds for oral administration may be formulated, for example, as push-fit capsules made of gelatin, as well as soft, sealed capsules made of gelatin and a coating such as glycerol or sorbitol. Push-fit capsules may contain platinum compounds mixed with filler or binders such as lactose or starches, lubricants such as talc or magnesium stearate, and, optionally, stabilizers. In soft capsules, the platinum compounds may be dissolved or suspended in suitable liquids, such as fatty oils, liquid paraffin, or liquid polyethylene glycol with or without stabilizers.

Compositions for parenteral administration include aqueous solutions of one or more platinum compounds of the invention. For injection, the platinum compounds may be formulated in aqueous solutions, such as in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the platinum compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents that increase the solubility of the platinum compounds to allow for the preparation of highly concentrated solutions.

For topical or nasal administration, penetrants appropriate to the particular barrier to be permeated are typically used in the formulation. Examples of these are 2-pyrrolidone, N-methyl-2-pyrrolidone, dimethylacetamide, dimethylformamide, propylene glycol, methyl or isopropyl alcohol, dimethylsulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences-Dekker); Harrys Cosmeticology (Leonard Hill Books).

For rectal administration, the compositions may be administered in the form of suppositories or retention enemas. Such compositions may be prepared by mixing the platinum compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

Compositions containing the platinum compounds of the present invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, e.g., sustained release or targeted release, by conventional means (e.g., coating).

Compositions containing the platinum compounds may be provided as a salt and can be formed with many acids, including but not limited to hydrochloric, sulfuric, acetic, lactic, tartaric, malic, succinic. Salts tend to be more soluble in aqueous or other protonic solvents than are the corresponding free base forms.

After compositions formulated to contain the platinum compounds and an acceptable carrier have been prepared, they can be placed in an appropriate container and labeled for use.

In other aspects, the present invention provides methods of manufacture of the platinum compounds.

The following examples are provided for the purpose of illustrating, not limiting, the invention.

EXAMPLES

Example 1

The Preparation of Cisplatin Tocopherol Succinate

In this example, the preparation of cisplatin tocopherol succinate is described.

Silver nitrate (2.78 g) was dissolved in water (30 ml) and added to cisplatin (2.5 gm) in a 50 ml conical flask. The contents were warmed to about 60° C. on a hotplate with rapid stirring until the silver chloride precipitation was complete and the mother liquor (supernatant) was almost colorless. (Note: when the precipitation is complete, the mother liquor looks completely colorless when stirring is stopped, indicating completion of reaction). The completion of the reaction (reaction of cisplatin) can be monitored by checking the filtrate by adding small amount of silver nitrate to see if any precipitation (AgCl) occurs (AgCl solubility in water is 1.93 mg/L). If precipitation occurs, the filtrate is again heated to 60° C. to ensure that there is no cloudiness or precipitation (AgCl) for about 30 min and then the solution is filtered again. The silver chloride was filtered off using a sintered glass filter and the precipitate washed with water to have a total/final volume of about 50 ml cisplatin nitrate solution.

Tocopherol succinate (vitamin E succinate, VESA) (4.41 gm) was dissolved in 60 ml methanol and the resulting solution was added to the cisplatin nitrate solution dropwise with stirring (the entire solution became cloudy white) and the reaction mixture left stirring in dark (covered with aluminum foil) for about 4 hours at which time the color of the reaction mixture changed to light yellow (yellowish cloudiness). The resulting solution was stirred overnight in the dark. The resulting solution was centrifuged and the precipitate, which was pale yellow/ash color, collected and dried in a vacuum oven. The resulting product, cisplatin tocopherol succinate, is soluble in methanol and acetone and is soluble in water at about 0.5 to about 1 mg/mL. Both the acetone and methanol solutions respond positive for the cisplatin test.

Example 2

The Preparation of Cisplatin Tocopherol Phosphate

In this example, the preparation of cisplatin tocopherol phosphate is described.

Silver nitrate (2.81 g) was dissolved in water (20 ml) and added to cisplatin (2.5 gm) in a 100 ml conical flask. The contents were warmed (~60° C.) on a hotplate with rapid stirring until the silver chloride precipitation was complete and the mother liquor (supernatant) was almost colorless. The silver chloride was filtered off using a sintered glass filter and the precipitate washed with water to have a total/final volume of 50 ml cisplatin nitrate solution. The filtrate was heated to about 60° C., checked for white precipitation (AgCl) and filtered off. This step was repeated two more times. The pH of this solution/filtrate was adjusted to about 6 using 1N aqueous KOH. Note: If the previous step of removing AgCl is not done carefully, the filtrate will turn black/brown due to oxidation of silver.

Tocophosphate (2.31 gm) was dissolved in 30 ml of water, pH adjusted to about 7.5 or 8.0 using 1N aqueous HCl, and the resulting solution was added to the cisplatin nitrate solution dropwise with stirring. The mixture was slowly heated on the hotplate until the cisplatin tocopherol phosphate crystallizes from the solution. After stirring overnight, the cisplatin tocopherol phosphate was collected by filtration. The filtrate was again heated and cooled, and the remaining product collected. The product had greenish color. The product is a dimer including two platinums per tocopherol phosphate.

Example 3

The Preparation of a Carboplatin Difolate Compound

In this example, the preparation of carboplatin difolate compound is described. The representative platinum compound can be prepared by converting folic acid to its N-hydroxysuccinimide ester, reacting the ester with diethylene triamine to provide a folate triamine, treating the folate triamine with potassium tetrachloroplatinate to provide a folate platinum chloride derivative, and then converting the platinum chloride derivative to a carboplatinum derivative by reaction with 1,1-cyclobutanedicarboxylic acid sodium salt to provide a carboplatin difolate compound.

Folate NHS-Ester.
1) Dissolve 4.41 g of folic acid 2.5 ml of triethylamine, and 2.3 g of N-hydroxysuccinimide (NHS) in 100 ml of dried DMSO.
2) Add 4.54 g of N,N'-dicyclohexylcarbodiimide to the solution.
3) Stir the reaction mixture in the dark at room temperature for overnight.
4) Remove insoluble byproduct, dicyclohexylurea, by filtration.
5) Reduce the volume of the reaction mixture by about 60% by distillation.
6) Precipitate NHS-folate by addition of 10×volume of 30% acetone/70% diethyl ether.
7) Filter and wash the product three times with 30% acetone/70% diethylether.
8) Dry the product under vacuum.
9) Final product: 5.1 g; yield: 80.2%.

Folate Triamine.
1) Dissolve 2.0 g of NHS-folate into 15 ml of dried DMSO at room temperature, and add the solution into 13 g of diethylene triamine.
2) Stir the solution for overnight.
3) Precipitate product by addition of 10×volume of 20% THF/80% diethyl ether.
4) Filter and wash the product three times with 20% THF/80% diethyl ether.
5) Dry product with vacuum.
6) Recrystallize the product in water/methanol/THF (volume ratio=1:1:1).

Folate Platinum Chloride.
1) Dissolve 1.36 g of potassium tetrachloroplatinate and 1.00 g of folate triamine into 20 ml of DMSO.
2) Stir the mixture for 24 hours at room temperature.
3) Precipitate product by addition of 10×volume of 50% THF/50% diethyl ether.
4) Filter and wash product with THF.
5) Dry product with vacuum.
6) Product: 2.40 g; yield: ~100%.

Carboplatin Difolate.
1) Add 1.14 g of folate platinum chloride and 0.68 g of $AgNO_3$ into 20 ml of DI water.
2) Stir mixture for 1 hour, and filter to remove AgCl precipitate.
3) Add 0.362 g of 1,1-cyclobutanedicarboxylic acid sodium salt into filtrate.
4) Stir the mixture at room for 4 hours.
5) Concentrate the mixture by removing water at room temperature.
6) Precipitate product by addition of THF.
7) Filter and wash the product with THF.
8) Dry the product with vacuum at room temperature.
9) Product: 1.20 g; yield: 93.0%.

Example 4

The Preparation and Characterization of Representative Polynuclear Platinum Compounds In this example, the preparation and characterization of representative polynuclear platinum compounds of the invention are described.

By varying the reaction conditions, temperature, pH, the polymer chain length of the polynuclear platinum compounds can be controlled. Low pH, high temperature conditions yield relatively high average molecular weight polymers (e.g., 100 kD or greater). High pH, low temperature conditions yield relatively low average molecular weight polymers (e.g., about 10 kD).

Polynuclear platinum compound preparation: high temperature, aqueous synthesis. Cisplatin (5 g) in 300 mL water was dissolved with stirring at about 75° C. to yield a clear yellow solution. To this solution was added $AgNO_3$ (2.82 g in 30 mL water) with stirring. The resulting solution was stirred for 30 minutes, cooled to 60° C., and stirring continued until silver chloride precipitation was complete. The reaction mixture was cooled and the silver chloride filtered using a sintered glass filter or disposable filtration units to provide a clear, transparent faintly colored solution. The filtrate was heated to 50° C. and lipoic acid (1.34 g in 60 mL methanol) was added. After the addition was complete, the reaction mixture was allowed to cool to room temperature and stirred overnight. A pale white (yellowish white) precipitate was formed. The mixture was centrifuged at 6300 rpm for 20 minutes at 22° C. and the supernatant was discarded. The precipitate was treated with water (about 50° C. for 30 minutes with stirring) to dissolve any free unreacted cisplatin/cisplatin nitrate. The product was again centrifuged at 6300 rpm for 20 minutes at 22° C. and the supernatant discarded. The precipitate was washed with acetone twice and centrifuged. The precipitate was then air dried to provide the product polynuclear platinum compound. This method provided a product having an average molecular weight of about 100 kD as determined by size exclusion chromatography.

Polynuclear platinum compound preparation: high temperature, saline synthesis. Cisplatin (5 g) in 300 mL saline solution was dissolved with stirring at about 70–75° C. to yield a clear yellow solution (about 2 hours to dissolve). The temperature was then reduced to 60° C. and lipoic acid (1.34 g dissolved in methanol) was added. The resulting solution was stirred at 60° C. for about 30 minutes, cooled to room temperature, and stirred for 48 hours. The reaction mixture was transparent to begin with and slowly become cloudy as the reaction proceeded.

The reaction mixture was centrifuged and the supernatant discarded. Saline solution was added to the precipitate and the reaction mixture was heated to 60° C., centrifuged, and the supernatant discarded. Water was added to the precipitate and the resulting mixture was stirred for about 15–20 minutes, centrifuged, and the supernatant decanted. This step was repeated to ensure removal of sodium chloride. Finally, the precipitate was washed with acetone twice with centrifugation to remove any organic impurities including unreacted lipoic acid. The precipitate was air dried at room temperature and then dried by vacuum without heating to provide the product. This method provided a product having an average molecular weight of greater than about 100 kD as determined by size exclusion chromatography.

Polynuclear platinum compound preparation: low temperature synthesis. To cisplatin (5 g) was added 2.82 g silver nitrate (dissolved in 100 mL water) with stirring. The reaction mixture was stirred at 70° C. for about 1 hour until silver chloride precipitation was complete. The heating was discontinued and silver chloride was removed by filtration using a sintered glass filter or disposable filteration units to provide a clear/transparent faintly colored solution. To this filtrate (maintained at about 5° C.) was added lipoic acid (3.43 g/100 ml 0.1 N aqueous NaOH) with stirring and without heating. Note: to dissolve lipoic acid, 10 mL of 1N aqueous NaOH was added to lipoic acid and then diluted to 100 mL to provide a final NaOH concentration of 0.1 N. After the addition was complete, the reaction mixture was yellow and clear. After about 1 hour at 5° C., the mixture remained yellow and clear. After 3 hours, the pH of the reaction mixture was lowered by the addition of 5N aqueous HCl resulting in the formation of an orange yellow precipitate. The precipitate was isolated by centrifuging and discarding the supernatant, and then washing the precipitate with water (10×50 mL) until the pH of the supernatant was neutral. The precipitate was then washed with acetone (5×50 mL). The precipitate was then dried under vacuum to provide the product polynuclear platinum compound. This method provided a product having an average molecular weight of about 7 kD as determined by size exclusion chromatography.

Polynuclear platinum compound characterization. Representative platinum compounds prepared as described above were characterized. All $^{13}C$ and $^1H$ nuclear magnetic resonance (NMR) absorptions are consistent with lipoic acid and the polymer structure illustrated in FIG. 6. The infrared (IR) data indicates a hydrated polymer of the modified structure without the two end groups: C—S—H and Pt—OH (see FIG. 6). Elemental analysis is indicative of the presence of the platinum lipoic acid moiety shown in FIG. 5.

Figure 8:
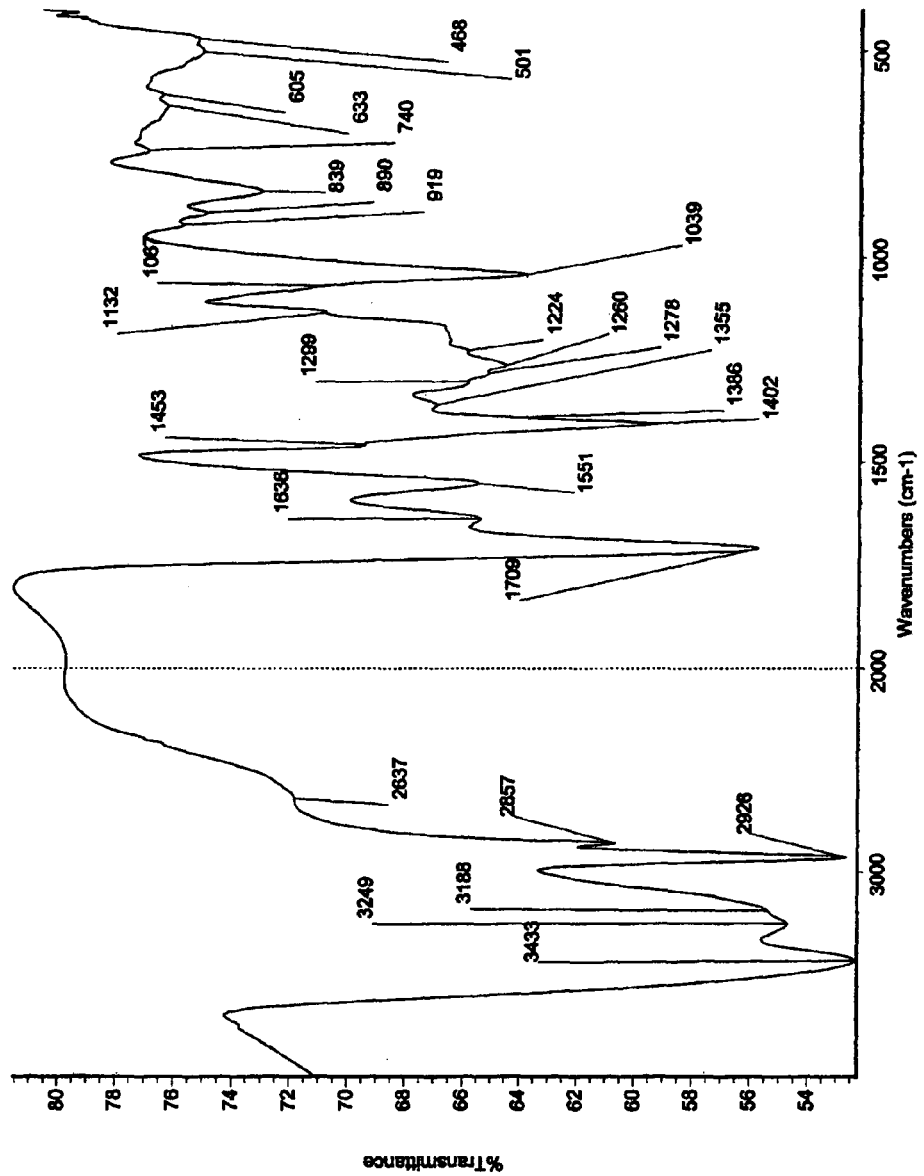
FIG. 8 is an infrared spectrum of a representative polynuclear platinum compound of the invention.

Infrared Spectral Properties. The region expected for S—H stretching is typically from 2560 to 2590 $cm^{-1}$, but there is no apparent infrared absorption seen in this spectrum. Note that the S—H stretching band is weak in the infrared and relatively strong in the Raman spectrum. Infrared bands at 2926, 2875, and 1453 $cm^{-1}$ indicate the presence of —$(CH_2)_n$—, and the band at 740 $cm^{-1}$ is reasonable for n=3. Bands near 2637 (broad), 1709, 1402, and 1260 $cm^{-1}$ are indicate the presence of hydrogen bonded carboxylic acid groups. Infrared absorptions for Pt—S, Pt—Cl, or Pt—N are expected to occur below 400 $cm^{-1}$ and may not be seen in this spectrum. The IR bands near 605 and 633 $cm^{-1}$ may result from C—S stretching from Pt—S—$CH_2$ and Pt—S—C—$(CH_2)$—. The infrared bands near 3249, 3188, and 1551 $cm^{-1}$ may result from antisymmetric, symmetric, and bending of the $NH_2$ group of Pt—$NH_2$. Infrared bands at 3433 and 1636 $cm^{-1}$ indicate the sample is either hydrated or $H_2O$ is present in the KBr, although it is possible that the end groups are not present (C—S—H and Pt—OH) and have formed another C—S—Pt group. One mole of water fit the elemental analysis provided. The IR data would support a hydrated polymer of the modified structure without the two end groups. The infrared spectrum is illustrated in FIG. 8.

Figure 9:
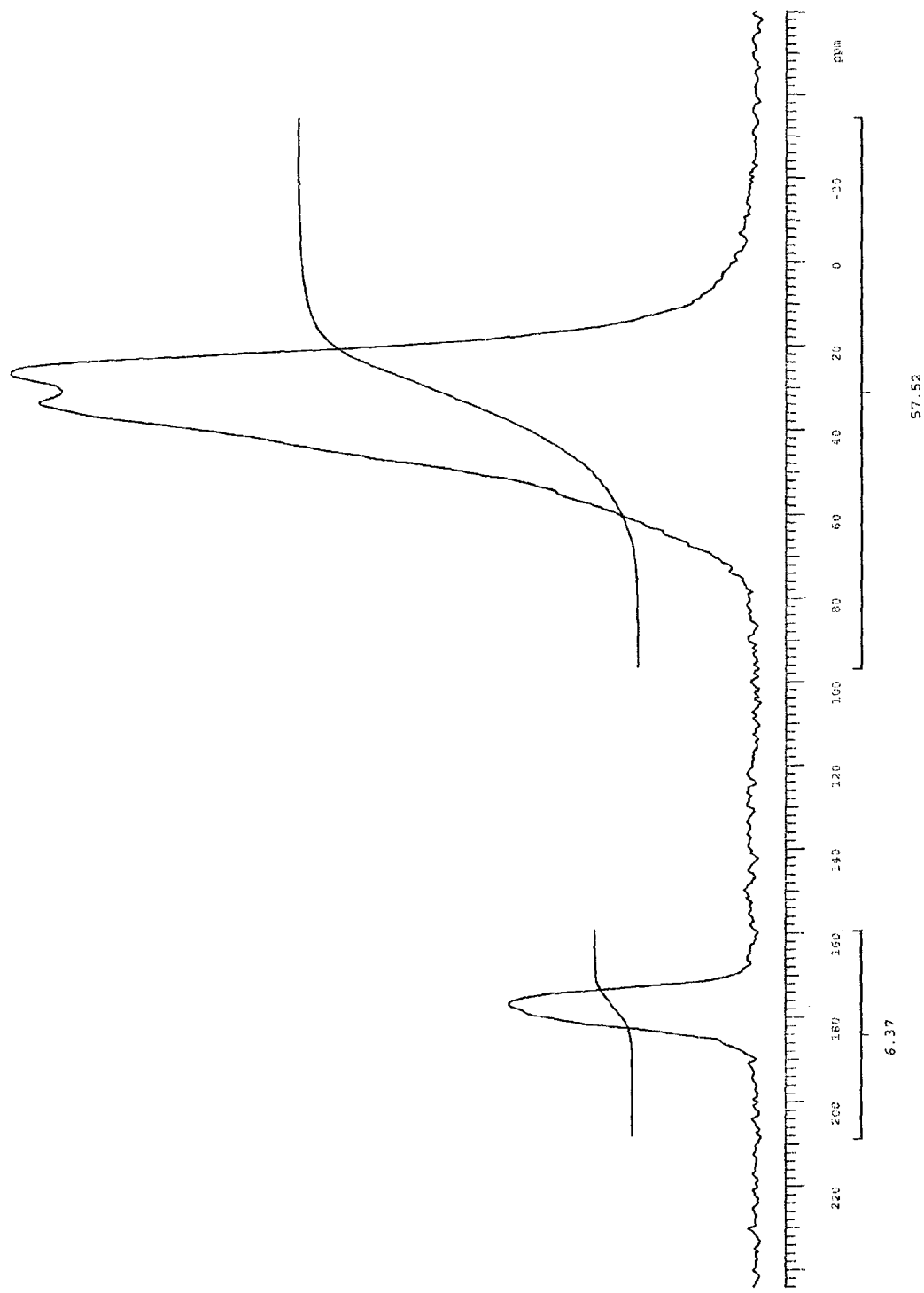
FIG. 9 is a $^{13}C$ nuclear magnetic resonance spectrum of a representative polynuclear platinum compound of the invention.

$^{13}C$ and $^1H$ Nuclear Magnetic Resonance Spectral Properties. Representative platinum compounds prepared as described above (high temperature/aqueous synthesis and low temperature synthesis) were characterized and had similar spectra. The solid state $^{13}C$ NMR spectrum exhibited a pattern that is simple and broad. All absorptions, including unresolved shoulders, lie at positions consistent with lipoic acid and the polymer structure. The $^{13}C$ spectra were obtained using a solid-state Varian Unity Plus-200 NMR spectrometer operating at 5.6 kHz. Lipoic acid shows carbon attached to thiol resonance at 63 ppm. The platinum lipoic acid polymer sample shows reduced intensity and broadened thiol carbon resonances in the 40–60 ppm region due to the carbon thiols bonded to platinum. The broadness in the peaks can be attributed to (1) the multiple resonances resulting from different orientations of the polymer in the crystal structure leading to differences in shielding and multiple resonances and to (2) the presence of repeating units in a polymer leading to the broadening of the peaks. The $^{13}C$ spectrum is illustrated in FIG. 9.

The $^1H$ NMR spectrum (NaOD) exhibited a pattern that is broad and simple, typical of polymer spectra. All absorptions are consistent with the —CH protons of lipoic acid and the polymer structure.

Elemental Analysis. Elemental analysis (Quantitative Technologies, Inc., Whitehouse, N.J.) for a representative platinum compound (low temperature synthesis) provided the following composition: C (20.92%), H (3.73%), Cl (7.72%), N (0.76%), O (10.45%), Pt (42.47%), and S (13.96%). The elemental analysis is indicative of the platinum lipoic acid moiety illustrated in FIG. 5.

Molecular Weight Analysis. The molecular weight was determined by a size exclusion chromatography method. In the method, polyethylene glycol molecular weight standards ranging from 3.3 kD to 100 kD were used. A representative polynuclear platinum compound exhibited a single peak in the chromatogram indicating a fairly narrow size distribution. The retention time was between that of the 10 kD and 3.35 kD polyethylene glycol standards. Although no linearity is certain when considering molecular weight and retention time, the molecular weight of the platinum compound prepared by the low temperature synthesis described above was estimated to be about 7 kD. The molecular weight of the platinum compound prepared by the high temperature/aqueous synthesis described above was estimated to be greater than about 100 kD.

Column conditions: 100% deionized water at 0.8 mL/min; refractive index mode of detection; a PolySep-GFC-P4000 column (Phenomenex, Part No. 00H-3144-KO). Other columns that are useful include PolySep-GFC-P3000 and PolySep-GFC-P5000 columns (Phenomenex).

Differential Scanning Calorimetry. Calorimetric measurements were performed using a Perkin-Elmer DSC-7 and Pyris data analysis system. About 5 mg sample was loaded into an aluminum hermetic capsule, heated to 250° C. at a rate of 10° C./minute, cooled at a rate of 10° C./minute in a nitrogen atmosphere. The same thermal program was used on the same sample for the second run. The DSC-7 instrument calibration was verified with NIST SRM 2220 tin.

The first run thermogram showed a stable baseline to 80° C. followed by a broad exotherm between 80° C. and 180° C. The DSC curve then exhibited an endotherm with a sharp leading edge and onset temperature of 206.4° C. This may be the result of decomposition and loss of the hermetic seal of the capsule. The subsequent cooling curve did not show a crystallization exotherm. The rescan on the same sample showed an increase in heat capacity without exotherm and a small residual endotherm with onset temperature of 190.6° C. The total weight of the sample and capsule changed from 29.70 mg to 29.20 mg after the two runs.

The results suggest a two-stage thermal decomposition: (1) loss of HS or HCl (known to be exothermic); and (2) loss of $CO_2$ (known to be endothermic). Loss of gas products results in a weight change.

Thermal Gravimetric Analysis. Weight loss measurements were carried out using a Perkin-Elmer Pyris 1 TGA. The TGA system is controlled by Perkin-Elmer Pyris program for data acquisition and analysis. The weight loss is expressed as a percentage of the initial sample weight and plotted against temperature. The TGA calibration was verified with calcium oxalate monohydrate, a standard reference material.

Sample (5–8 mg) was loaded into the TGA immediately to avoid absorption or desorption of moisture from the atmosphere. The measurements were carried out from room temperature to 900° C. at 10° C./minute in an inert nitrogen atmosphere.

The TGA curve exhibited three weight loss steps. The weight loss started at room temperature and leveled off at 100° C. (step 1). The weight loss in this temperature range is 3%. The weight loss may be due to vaporization of associated water. Further weight loss above about 100° C. can be attributed to the decomposition of the compound itself. The sample lost 10% of its weight up to 250° C. This result is consistent with the DSC results. The weight loss was 31% between 100° C. and 250° C. (step 2) and 10% between 500° C. and 900° C. (step 3). The total weight loss was 44%. The changes suggest decomposition of the compound and are consistent with the DSC results.

Example 5

Cytotoxicity Assays Using a Representative Platinum Compound

This Example describes comparative cytotoxicity assays using cisplatin, carboplatin, and a representative platinum compound of the invention (S-9168) and a panel of cancer cell lines.

Methods. NCI-H460, HCT-15, OVCAR-3, CACO-2, MCF-7, HT-29, and HCT-116 cells were inoculated into 96 well microtiter plates in 100 microliters of medium at plating densities ranging from 5000 to 40000 cells/well, as given by NCI tables. After cell inoculation, the microtiter plates were incubated at 37° C., 5% $CO_2$, 95% air, and 100% relative humidity for 24 hours. After 24 hours, 2 control plates of each cell line (time zero controls) were fixed by the addition of 30% trichloroacetic acid (TCA, final TCA concentration is 10% w/v).

S-9168 was solubilized in saline. Cisplatin (Saiquest I), carboplatin (Spectrum), and S-9168 were diluted in media to twice the maximum final test concentration. Additional 4, 10 fold, or ½ log serial dilutions were made to provide a total of five drug concentrations plus controls. Aliquots of 100 microliters of different drug dilutions were added to the appropriate microtiter wells already containing 100 microliters of medium. Following drug addition, the plates were incubated for an additional 48 hours under the same conditions provided above.

The assays were terminated by the addition of cold TCA as described above for the time zero controls. The plates were then incubated at 4° C. for at least 60 minutes to fix the cells to the bottom of the plate. After fixation, the supernatant was discarded, and the plates were washed five times with water and air dried for 12–24 hours at room temperature. 100 microliters of 0.4% (w/v) Sulfarhodamine B dissolved in 1% acetic acid was added to each well, and the plates were incubated for 10 minutes at room temperature to stain the fixed cells. After staining, unbound dye was removed by washing five times with 1% acetic acid and the plates were allowed to air dry for 12–24 hours at room temperature. The bound stain was subsequently solubilized with 100 microliters of 10 mM Trizma base, shaking until all the bound stain is in solution. The absorbance of each plate was read on an automated plate reader at a wavelength of 492 nm and the $GI_{50}$ was determined for each drug. The $GI_{50}$ value is the concentration of drug that causes 50% growth inhibition with correction for the cell count at time zero. Thus, $GI_{50}$ is the concentration of test drug (moles/l) where 100×(optical density of test well after a 48 hour period of exposure to test drug minus optical density at time zero)/(control optical density minus optical density at time zero) =50.

Results. The results of 9 different cytotoxicity assays are presented in Table 1. The $GI_{50}$ values are provided as milligrams of platinum per milliliter instead of moles of test drug per liter. For all cell lines tested, the $GI_{50}$ values for cisplatin and carboplatin were similar to those previously determined (NCI values). For cell lines NCI-H460, HCT-15, OVCAR, HT-29, and HCT-116, the $GI_{50}$ values obtained for S-9168 were similar to those for carboplatin. The $GI_{50}$ value for S-9168 in MCF-7 cells was between those obtained for cisplatin and carboplatin.

TABLE 1

$GI_{50}$ Values for Cisplatin, Carboplatin, and S-9168

| Cell line | Assay | Cisplatin Pt mg/ml (log) | Carboplatin Pt mg/ml (log) | S-9168 Pt mg/ml (log) |
|---|---|---|---|---|
| NCI-H460 | Assay 1 | $1.0557 \times 10^{-7}$ (−6.98) | | $2.2978 \times 10^{-6}$ (−5.64) |
| | Assay 2 | | $1.0855 \times 10^{-5}$ (−4.96) | $1.5996 \times 10^{-5}$ (−4.79) |
| | Assay 3 | | | $1.1489 \times 10^{-5}$ (−4.94) |
| | Assay 4 | | | $1.3952 \times 10^{-5}$ (−4.86) |

TABLE 1-continued

GI$_{50}$ Values for Cisplatin, Carboplatin, and S-9168

| Cell line | Assay | Cisplatin Pt mg/ml (log) | Carboplatin Pt mg/ml (log) | S-9168 Pt mg/ml (log) |
|---|---|---|---|---|
| | NCI values | 1.19 × 10$^{-7}$ (−6.92) | 6.1642 × 10$^{-6}$ (−5.21) | |
| HCT-15 | Assay 2 | | 4.8534 × 10$^{-5}$ (−4.31) | |
| | Assay 5 | 2.2368 × 10$^{-7}$ (−6.65) | | 1.1138 × 10$^{-4}$ (−3.95) |
| | NCI values | 1.5017 × 10$^{-6}$ (−5.82) | 4.9002 × 10$^{-5}$ (−4.31) | |
| OVCAR-3 | Assay 6 | | 1.5101 × 10$^{-5}$ (−4.82) | 2.3584 × 10$^{-5}$ (−4.63) |
| | NCI value | 4.7493 × 10$^{-7}$ (−6.32) | 1.2309 × 10$^{-5}$ (−4.91) | |
| MCF-7 | Assay 2 | 7.9009 × 10$^{-6}$ (−5.10) | | |
| | Assay 7 | 7.2146 × 10$^{-7}$ (−6.14) | | 1.4607 × 10$^{-6}$ (−5.84) |
| | NCI values | 5.9744 × 10$^{-7}$ (−6.22) | 2.4579 × 10$^{-5}$ (−4.61) | |
| HT-29 | Assay 8 | 1.0138 × 10$^{-6}$ (−5.99) | | 7.9578 × 10$^{-5}$ (−4.09) |
| | NCI values | 1.5012 × 10$^{-6}$ (−5.82) | 3.8917 × 10$^{-5}$ (−4.41) | |
| HCT-116 | Assay 9 | 7.4907 × 10$^{-7}$ (−6.13) | | 5.6038 × 10$^{-5}$ (−4.25) |
| | NCI values | 7.5266 × 10$^{-7}$ (−6.12) | 3.0919 × 10$^{-5}$ (−4.51) | |

Example 6

Creatinine Levels After Administration of Cisplatin or a Representative Platinum Compound This example compares the creatinine level as a measure of renal function after a single dose of cisplatin and a representative platinum compound of the invention (S-9168).

Methods. Three groups of two rats were cannulated in the jugular vein and allowed to recover for approximately 24 hours. Group 1 rats were dosed with 8 mg/kg cisplatin (5.2 mg platinum/kg), group 2 rats were dosed with 8 mg/kg S-9168 (4.2 mg platinum/kg), and group 3 rats were dosed with saline. Blood samples (1.8 ml) were taken via the jugular vein canal before treatment (day 0) and 1, 2, 3, and 4 days after treatment, spun at 8000 rpm. for 2 minutes, and the plasma was removed. Creatinine assays were performed using the Sigma Creatinine Kit (Sigma Diagnostics Co., St. Louis, Mo.; Cat. No. 555-A) according to the Sigma creatinine assay protocol, in which the difference in color intensity at 500 nm of a sample containing creatinine and alkaline picrate solution before and after acidification is measured. The limit of linearity for the UV spectrophotometer was established by using the calibration curve procedure in the Sigma creatinine assay protocol.

Results. The average creatinine levels (mg/dl) for each group of rats, and the corresponding standard deviations (std. dev.), are shown in Table 2. The average creatinine levels in rats administered cisplatin more than doubled between day 0 to day 4, whereas the average creatinine levels administered S-9168 or saline dropped between day 0 to day 4.

TABLE 2

Creatinine Levels after Treatment with Cisplatin, S-9168, and Saline

| Day | Cisplatin mg/dl (std. dev.) | S-9168 mg/dl (std. dev.) | Saline mg/dl (std. dev.) |
|---|---|---|---|
| 0 | 0.745835 (0.015309) | 0.742095 (0.030116) | 0.70851 (0.105104) |
| 1 | 0.715775 (0.128149) | 0.77506 (0.029232) | 0.687055 (0.004589) |
| 2 | 0.785795 (0.044838) | 0.708825 (0.023455) | 0.8113 (0.030038) |
| 3 | 0.91319 (0.137843) | 0.844105 (0.104447) | 0.676175 (0.015054) |
| 4 | 1.573335 (0.058937) | 0.561515 (0.038205) | 0.498575 (0.009709) |

Example 7

Creatinine Levels After Administration of Cistlatin Carboplatin, or a Representative Platinum Compound This example compares the creatinine level as a measure of renal function after treatment with cisplatin, carboplatin, and a representative platinum compound of the invention (S-9168).

Methods. Four groups of eight rats were cannulated as described in Example 6. Three groups of rats were dosed with a drug: group 1 rats were dosed with 8 mg/kg cisplatin (5.2 mg platinum/kg), group 2 rats were dosed with 9.9 mg/kg carboplatin (5.2 mg platinum/kg), and group 3 rats were dosed with 19.6 mg/kg S-9168 (10.19 mg platinum/kg). The fourth group of rats was dosed with saline. Two rats in each group were sacrificed on days 4, 6, and 8 after treatment and 2 ml of blood were withdrawn. The blood sample was spun at 8000 rpm. for 2 minutes and the plasma was removed. Creatinine assays were performed as described in Example 6.

Results. The average creatinine levels (mg/dl) for each group of rats, and the corresponding standard deviations (std. dev.), are shown in Table 3. The average creatinine levels in rats administered S-9168 were similar to those of rats administered carboplatin or saline, and considerably less than those administered cisplatin.

TABLE 3

Creatinine Levels after Treatment with Cisplatin, Carboplatin, and S-9168

| Day | Cisplatin mg/dl (std. dev.) | Carboplatin mg/dl (std. dev.) | S-9168 mg/dl (std. dev.) | Saline mg/dl (std. dev.) |
|---|---|---|---|---|
| 4 | 4.390618 (0.624184) | 0.6658849 (0.0569907) | 0.74968 (0.077797) | 0.633262 (0.2352) |
| 6 | 2.157198 (1.117614) | 0.7038911 (0.3730883) | 0.633269 (0.061906) | 0.630934 (0.045398) |
| 8 | 0.911576 (0.100609) | 0.540193 (0.0238734) | 0.555868 (0.020463) | 0.559486 (0.001705) |

Example 8

BUN Levels After Administration of Cisplatin or a Representative Platinum Compound This example compares the blood urea nitrogen (BUN) levels as a measure of renal function after treatment with cisplatin, carboplatin, and a representative platinum compound of the invention (S-9168).

Methods. Four groups of eight rats were cannulated as described in Example 6. Three groups of rats were dosed with a drug: group 1 rats were dosed with 8 mg/kg cisplatin (5.2 mg platinum/kg), group 2 rats were dosed with 9.9 mg/kg carboplatin (5.2 mg platinum/kg), and group 3 rats were dosed with 19.6 mg/kg S-9168 (10.19 mg platinum/kg). The fourth group of rats was dosed with saline. Two rats in each group were sacrificed on days 4, 6, and 8 after treatment and 2 ml of blood were withdrawn. The blood sample was spun at 8000 rpm. for 2 minutes and the plasma was removed. BUN assays were performed using the Sigma Blood Urea Nitrogen Kit (Sigma Diagnostics Co., St. Louis, Mo.; Cat. No. 535-A).

Results. The average BUN levels (mg/dl) for each group of rats, and the corresponding standard deviations (std. dev.), are shown in Table 4. The average BUN levels in rats administered S-9168 were similar to those of rats administered carboplatin or saline, and considerably less than those administered cisplatin.

TABLE 4

BUN Levels after Treatment with Cisplatin, Carboplatin, and S-9168

| Day | Cisplatin mg/dl (std. dev.) | Carboplatin mg/dl (std. dev.) | S-9168 mg/dl (std. dev.) | Saline mg/dl (std. dev.) |
| --- | --- | --- | --- | --- |
| 4 | 225.8189655 (46.75438803) | 28.92241379 (2.255426802) | 19.35344828 (0.670532293) | 23.23275862 (10.91138912) |
| 6 | 200.5603448 (108.6871889) | 21.59482759 (3.352661463) | 26.20689655 (1.828724434) | 22.67241379 (0.487659849) |
| 8 | 100.3017241 (53.70354088) | 25.51724138 (1.462979547) | 19.61206897 (0.182872443) | 23.27586207 (0.609574811) |

While the preferred embodiment of the invention has been illustrated and described, it will be appreciated that various changes can be made therein without departing from the spirit and scope of the invention.

The invention claimed is:

1. A platinum compound, comprising two dihydrolipoic acid moieties bridged by a platinum atom through dihydrolipoic acid sulfur atoms.

2. The compound of claim 1, wherein the compound is a polynuclear platinum compound.

3. A platinum compound including a moiety having the formula:

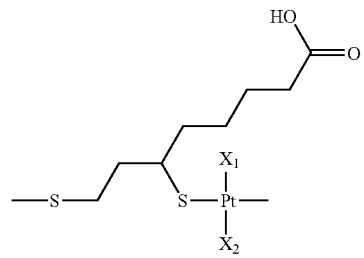

wherein $X_1$ and $X_2$ are independently selected from chloro, hydroxy, and amino; or pharmaceutically acceptable salts thereof.

4. The compound of claim 3, wherein the compound is a polynuclear platinum compound.

5. A platinum compound having the formula:

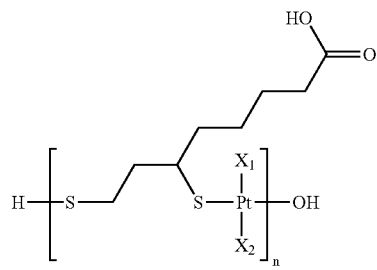

wherein $X_1$ and $X_2$ are independently selected from chloro, hydroxy, and amino;

wherein n is 10–200;

or pharmaceutically acceptable salts thereof.

6. The compound of claim 5, wherein n=10–20.

7. The compound of claim 5, wherein n=15.

8. A composition, comprising an amount of a compound of claim 1 effective to treat a proliferative disease in a human or animal subject when administered thereto, together with a pharmaceutically acceptable carrier.

9. The composition of claim 8 further comprising at least one additional agent for the treatment of cancer.

10. The composition of claim 9, wherein the at least one additional agent for the treatment of cancer is selected from flutamide, luprolide, tomoxifen, daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, streptozocin, bleomycin, dactinomycin, idamycin, medroxyprogesterone, estramustine, ethinyl estradiol, estradiol, leuprolide, megestrol, octreotide, diethylstilbestrol, chlorotrianisene, etoposide, podophyllotoxin, goserelin, melphalan, chlorambucil, methlorethamine, thiotepa, betamethasone, dicarbazine, asparaginase, leucovorin, mitotane, vincristine, vinbiastine, and taxanes.

11. A method for treating a cancer disorder in a human or animal subject, comprising administering to the human or animal subject a composition comprising an amount of a compound of claim 1 effective to treat the human or animal subject.

12. The method of claim 11, wherein the composition further comprises at least one additional agent for the treatment of cancer.

13. The method of claim 12, wherein the at least one additional agent for the treatment of cancer is selected from flutamide, luprolide, tomoxifen, daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, streptozocin, bleomycin, dactinomycin, idamycin, medroxyprogesterone, estramustine, ethinyl estradiol, estradiol, leuprolide, megestrol, octreotide, diethylstilbestrol, chlorotrianisene, etoposide, podophyllotoxin, goserelin, melphalan, chlorambucil, methlorethamine, thiotepa, betamethasone, dicarbazine, asparaginase, leucovorin, mitotane, vincristine, vinblastine, and taxanes.

14. The method of claim 11, wherein the cancer is at least one of primary melanoma, metastatic melanoma, thymoma, lymphoma, sarcoma, NSC lung cancer, SC lung cancer, gastric cancer, liver cancer, non-Hodgkin's lymphoma, Hodgkins lymphoma, leukemia, testicular cancer, uterine cancer, cervical cancer, bladder cancer, kidney cancer, colon cancer, colorectal cancer, breast cancer, prostate cancer, ovarian cancer, or pancreatic cancer.

15. A compound of claim 1 for use in the treatment of cancer.

* * * * *

UNITED STATES PATENT AND TRADEMARK OFFICE
CERTIFICATE OF CORRECTION

PATENT NO. : 7,038,071 B2  Page 1 of 1
APPLICATION NO. : 10/622007
DATED : May 2, 2006
INVENTOR(S) : M. Lal It is certified that error appears in the above-identified patent and that said Letters Patent is hereby corrected as shown below:

| COLUMN | LINE | ERROR |
|---|---|---|
| (56) Pg. 1, col. 2 | Refs. Cited (Other Publs., Item 7) | "α-Tocherol" should read --α-Tocopherol-- |
| (56) Pg. 1, col. 2 | Refs. Cited (Other Publs., Item 7) | "*104*(2):243,250," should read --*104*(2):243, 250,-- |
| (56) Pg. 1, col. 2 | Refs. Cited (Other Publs., Item 7) | "4H$_2$O)", *Polyhedron 15*(3)439-446," should read --4H$_2$O", *Polyhedron 15*(3):439-446,"-- |
| 20 (Claim 10, | 42 line 10) | "vinbiastine," should read --vinblastine,-- |

Signed and Sealed this

Twenty-sixth Day of September, 2006

JON W. DUDAS
*Director of the United States Patent and Trademark Office*